United States Patent
Isitani et al.

(10) Patent No.: US 7,122,103 B2
(45) Date of Patent: Oct. 17, 2006

(54) AIR/FUEL RATIO DETECTION APPARATUS

(75) Inventors: Shigeo Isitani, Gunma (JP); Futoshi Ichiyanagi, Gunma (JP); Yasuji Orimo, Gunma (JP); Chiharu Katsuyama, Gunma (JP)

(73) Assignee: Hitachi Ltd., Tokyo-to (JP)

(*) Notice: Subject to any disclaimer, the term of this patent is extended or adjusted under 35 U.S.C. 154(b) by 731 days.

(21) Appl. No.: 10/401,560

(22) Filed: Mar. 31, 2003

(65) Prior Publication Data
US 2003/0188967 A1    Oct. 9, 2003

(30) Foreign Application Priority Data
Mar. 29, 2002    (JP)    ............... 2002-096102

(51) Int. Cl.
*G01N 27/41*    (2006.01)
(52) U.S. Cl. .................... 204/425; 204/429
(58) Field of Classification Search ............... 204/424, 204/425, 426, 429; 205/784.5, 785; 73/23.31, 73/23.32
See application file for complete search history.

(56) References Cited

U.S. PATENT DOCUMENTS

| | | | |
|---|---|---|---|
| 4,642,174 A * | 2/1987 | Shibata ........................ 204/408 |
| 4,718,999 A * | 1/1988 | Suzuki et al. ................ 204/406 |
| 4,882,033 A * | 11/1989 | Shibata et al. ............... 204/425 |
| 4,980,042 A | 12/1990 | Shiomi et al. | |
| 5,686,654 A | 11/1997 | Friese et al. | |
| 5,935,399 A | 8/1999 | Hiromi et al. | |
| 5,972,200 A | 10/1999 | Kim | |

FOREIGN PATENT DOCUMENTS

| | | |
|---|---|---|
| EP | 0 125 069 A1 | 11/1984 |
| EP | 0 580 206 A1 | 1/1994 |
| JP | 61-10762 | 1/1986 |
| JP | 9-509747 | 9/1997 |

* cited by examiner

*Primary Examiner*—Kaj K. Olsen
(74) *Attorney, Agent, or Firm*—Sughrue Mion, PLLC (57) ABSTRACT

The invention relates to an air/fuel ratio detection apparatus for a gas. This apparatus includes (a) a heater portion having an elongate cylindrical shape; (b) a solid electrolyte layer surrounding the heater portion and activated by heat to conduct oxygen ions therethrough; (c) a first electrode positioned between the heater portion and the solid electrolyte layer; (d) second and third electrodes in contact with an outer surface of the solid electrolyte layer and away from each other; (e) a first voltage applying device for applying a first voltage between the first and second electrodes; (f) a second voltage applying device for applying a second voltage between the first and third electrodes, the second voltage being higher than the first voltage; and (g) a diffusion layer made of a porous material and covering the second electrode to adjust transmission of the gas to the second electrode.

18 Claims, 10 Drawing Sheets

AIR/FUEL RATIO DETECTION APPARATUS

BACKGROUND OF THE INVENTION

The present invention relates to an air/fuel ratio detection apparatus for determining air/fuel ratio of, for example, automotive engines from oxygen concentration or the like of exhaust gas.

In general, automotive engines and the like are provided with an air/fuel ratio sensor (oxygen sensor) in the middle of exhaust pipe or the like for detecting oxygen concentration or the like of exhaust gas.

The air/fuel ratio sensor outputs air/fuel ratio detection signal. Based on this signal, it is possible to conduct a feed-back control of the amount of fuel injection, thereby achieving stoichiometric air/fuel ratio (A/F=14.7) or lean air/fuel ratio (A/F≧15). With this, it is possible to improve engine combustion efficiency and fuel consumption.

There are such conventional air/fuel ratio sensors, which are plate-like in shape (see Japanese Patent Laid-open (Kokai) Publication Showa 61(1986)-10762 and Japanese Patent Laid-open (Kohyo) Publication Heisei 9(1997)-509747 corresponding to U.S. Pat. No. 5,686,654). These plate-like air-fuel ratio sensors include a heater portion and a solid electrolyte layer and a diffusion layer, which are formed on the heater portion.

There are recent demands for the improvement in productivity of air/fuel ratio sensors and for freedom in the direction of installation of air/fuel ratio sensors. With this freedom, it becomes possible to improve the accuracy for detecting oxygen concentration and the like and thereby to properly control the amount of fuel injection and stabilize the engine control. Furthermore, there are recent demands for the rapid temperature increase of the heater portion of air/fuel ratio sensors after the engine starts. With this rapid increase, it becomes possible to shorten the period of time required for activating the solid electrolyte layer and the like, thereby shortening the period of time required for enabling the measurement of oxygen concentration and the like. This makes it possible to properly conduct a feedback control of the amount of fuel injection, based on the signal from air/fuel ratio sensors, at an early stage after the engine starts.

SUMMARY OF THE INVENTION

It is an object of the present invention to provide an air/fuel ratio detection apparatus, which makes it possible to improve accuracy and stability in detecting oxygen concentration of exhaust gas.

It is another object of the present invention to provide an air/fuel ratio detection apparatus, which is simple in structure and is improved in workability during its production.

According to the present invention, there is provided an air/fuel ratio detection apparatus for a gas, comprising:

a heater portion that has an elongate cylindrical shape and heats by applying electricity to the heater portion from an outside;

a solid electrolyte layer formed on and entirely surrounding periphery of the heater portion, the solid electrolyte layer being activated by heat from the heater portion to conduct oxygen ions through the solid electrolyte layer;

a first electrode that is positioned between the heater portion and the solid electrolyte layer and is in contact with an inner surface of the solid electrolyte layer;

second and third electrodes that are in contact with an outer surface of the solid electrolyte layer and are away from each other such that the solid electrolyte layer is interposed between the first and second electrodes and between the first and third electrodes;

a first voltage applying device for applying a first voltage between the first and second electrodes;

a second voltage applying device for applying a second voltage between the first and third electrodes, the second voltage being higher than the first voltage; and a diffusion layer made of a porous material, the diffusion layer covering the second electrode to adjust transmission of the gas to the second electrode.

The other objects and features of this invention will become understood from the following description with reference to the accompanying drawings.

DESCRIPTION OF THE PREFERRED EMBODIMENTS

Figure 1:
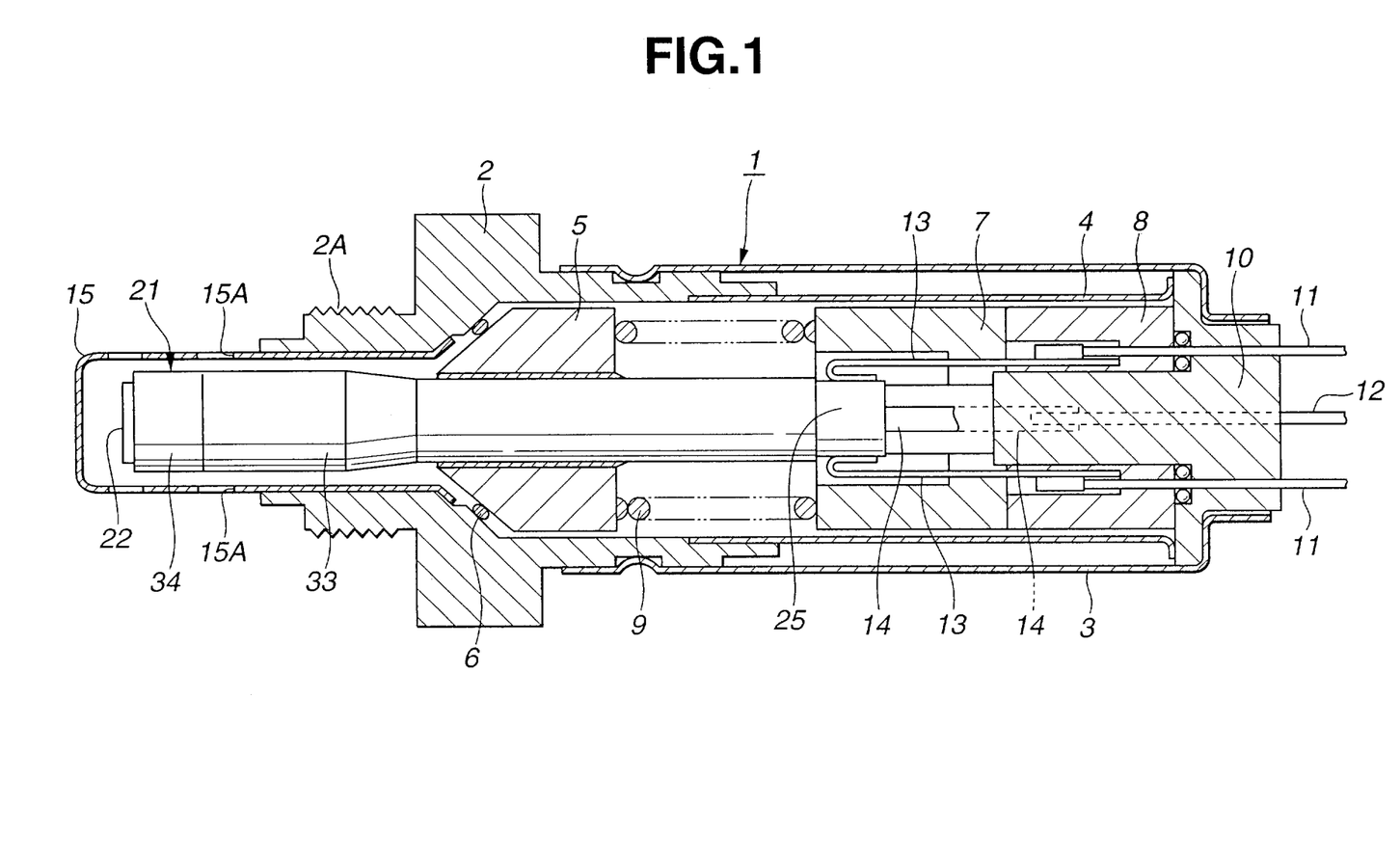
FIG. 1 is a longitudinal section showing an air/fuel ratio sensor formed with an air/fuel ratio detection device according to a first embodiment of the present invention.

As stated above, an air/fuel ratio detection apparatus according to the present invention has a heater portion that has an elongate cylindrical shape. Thus, it is possible to sequentially form a solid electrolyte layer, first to third electrodes, a diffusion layer and the like on the periphery of the heater portion using technique such as curved surface printing. Therefore, it is possible to form the air/fuel ratio detection apparatus as a whole into an elongate cylindrical shape, as shown in FIG. 1. This elongate cylindrical shape can provide more freedom in selecting the direction of installation of the air/fuel ratio detection apparatus. This makes it possible to detect oxygen concentration and the like of exhaust gas with a stable accuracy. Furthermore, it becomes possible to have an enlarged heating surface area of the heater portion for heating the solid electrolyte layer. With this, it becomes possible to efficiently transmit heat from the heater portion towards the solid electrolyte layer and the like. Therefore, it becomes possible to shorten the period of time for increasing the temperature of the heater portion, thereby activating the solid electrolyte layer early. This makes it possible to stably and accurately detect or determine air/fuel ratio at an early stage after the engine starts, thereby instantly conducting feedback control. Furthermore, it is not necessary to introduce the air (as a standard) into the inside of the air/fuel ratio detection device. Therefore, the air/fuel ratio detection apparatus is simplified in structure, thereby improving workability for producing the same. Furthermore, the heater portion is reduced in electric power consumption.

Furthermore, the air/fuel ratio detection apparatus is clearly made by its elongate cylindrical shape to have a smaller size, as compared with conventional plate-like air/fuel ratio detection apparatuses. Furthermore, it is possible to arrange the first to third electrodes such that the first electrode is opposed to the second and third electrodes with an interposal of a solid electrolyte layer in a radial direction. With this, it becomes possible to provide the first to third electrodes with a large electrode surface and with a short distance therebetween to reduce electrical resistance. Furthermore, it is possible to make the air/fuel ratio detection apparatus smaller in diameter. Still furthermore, it is possible to form a diffusion layer on the peripheral side of the solid electrolyte layer. With this, it becomes possible to easily correct deviation in porosity of the diffusion layer and to improve yield in the production.

By applying the above-mentioned first and second voltages (first voltage<second voltage) respectively between the first and second electrodes and between the first and third electrodes, it is possible to detect a diffusion limiting current (pumping current) of oxygen passing through the diffusion layer when the exhaust gas is in a lean condition and to detect a limiting current as the oxygen current necessary for oxidizing combustible gas components passing through the diffusion layer when the exhaust gas is in a rich condition.

With reference to FIGS. 1–14, an air/fuel ratio detection apparatus (air/fuel ratio or oxygen sensor) according to a first embodiment of the present invention used, for example, for a wide range air/fuel ratio sensor attached to the exhaust pipe of an automotive engine will be described in detail in the following.

As is seen from FIG. 1, designated by numeral 1 is a casing of the first air/fuel ratio sensor. This casing 1 comprises (a) cylindrical holder 2 having external threaded portion 2A, (b) cylindrical cap 3 that is integrally secured to a base portion of holder 2, and (c) guiding tube 4 that is disposed to be concentric with cap 3 and is positioned between the after-mentioned sealing cap 10 and holder 2.

Each of holder 2, cap 3 and guiding tube 4 can be made of a metal material such as stainless steel. External threaded portion 2A is threadedly engaged with the exhaust pipe such that the after-mentioned air/fuel ratio detection device 21 protrudes into the inside space of exhaust pipe.

Designated by numeral 5 is an insulating support that is disposed in a void space defined by holder 2 with an interposal of metal seal ring 6. Insulating support 5 has a generally cylindrical shape and a cylindrical opening for receiving air/fuel ratio detection device 21 and is made of a ceramic material (e.g., aluminum oxide ($Al_2O_3$)). In fact, air/fuel ratio detection device 21 is secured to the inner cylindrical wall of insulating support 5 by an inorganic bond or the like. Thus, air/fuel ratio detection device 21 is positioned at a proper position in casing 1 by insulating support 5 and is electrically and thermally insulated by insulating support 5.

Designated by numerals 7, 8 are insulating cylindrical members disposed in the inside space of guiding tube 4. Each of these cylindrical members 7, 8 is made of a ceramic material (e.g., aluminum oxide (hereinafter referred to as alumina)) and keeps the after-mentioned contact plates 13, 14 and the like in an insulated condition against the casing 1.

Designated by numeral 9 is a spring (as an elastic member) that is positioned in the inside of casing 1 and is sandwiched between insulating support 5 and insulating cylindrical member 7. Spring 9 biases insulating support 5 toward holder 2 and serves to prevent a direct transmission of vibration, shock and the like from an outside to air/fuel ratio detection device 21 through casing 1.

Designated by numeral 10 is a seal cap for closing a base end of cap 3. Seal cap 10 has a stepped cylindrical shape and is made of a heat-resistant resin material (e.g., polytetrafluoroethylene (PTFE)). Insulating cylindrical members 7, 8 and the like are positioned at proper positions in the inside of casing 1 with a biasing force of spring 9.

Lead wires 11, 11 for detecting air/fuel ratio and lead wires 12, 12 (only one is shown in FIG. 1) for energizing the heater portion are inserted into the seal cap 10. Lead wires 11, 11 are electrically connected with contact plates 13, 13, and lead wires 12, 12 are electrically connected with contact plates 14, 14.

Designated by numeral 15 is a protector formed on holder 2 of casing 1. Protector 15 is formed into a cylindrical shape by using a heat-resistant metal plate or the like. Protector 15 is attached at its base portion to holder 2 to cover an end portion of air/fuel ratio detection device 21. With this, the end portion of protector 15 protrudes from holder 2 in its axial direction.

Protector 15 is formed at its end portion with a plurality of openings 15A for guiding the exhaust gas (flowing through the exhaust pipe) toward the end portion of air/fuel ratio detection device 21.

Figure 2:
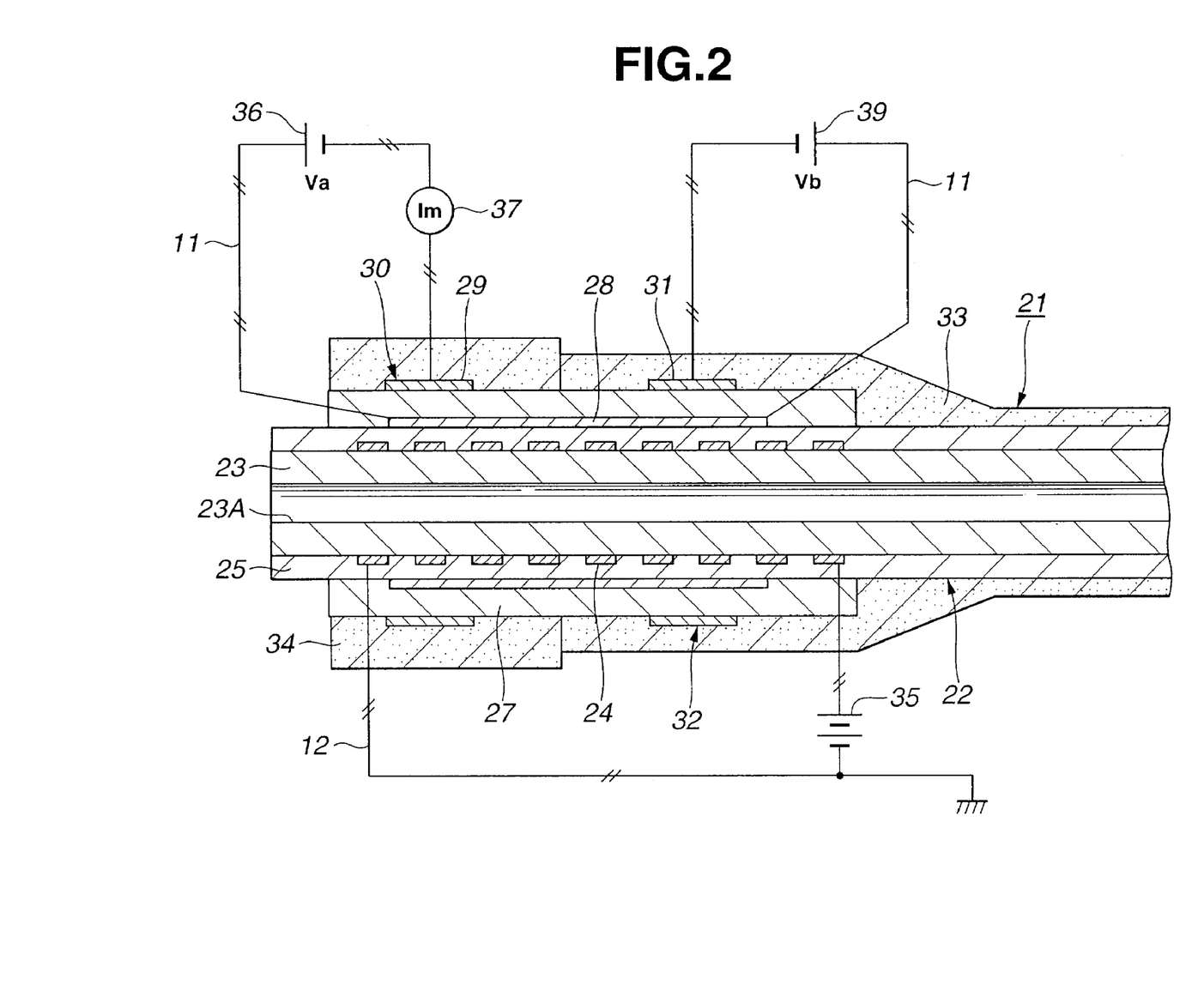
FIG. 2 is a longitudinal section showing the air/fuel ratio detection device of FIG. 1.
Figure 6:
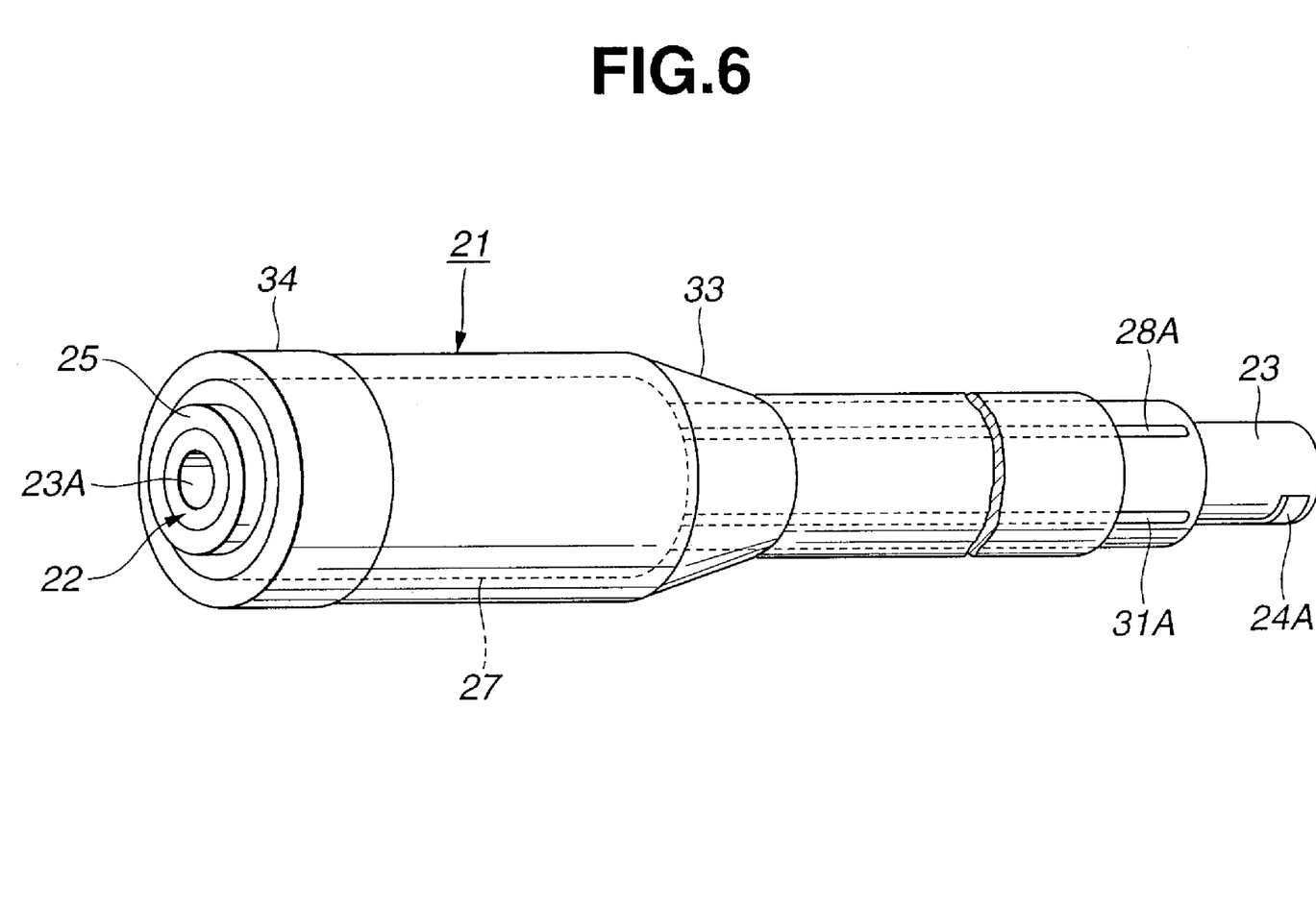
FIG. 6 is a perspective view showing a condition in which the further parts of FIG. 5 have been assembled together.

Air/fuel ratio detection device 21 is fixed in the inside of holder 2 by insulating support 5, and the end portion of device 21 protrudes from holder 2 in the axial direction. As shown in FIGS. 2 and 6, air/fuel ratio detection device 21 comprises heater portion 22, solid electrolyte layer 27 and diffusion layer 34.

Figure 3:
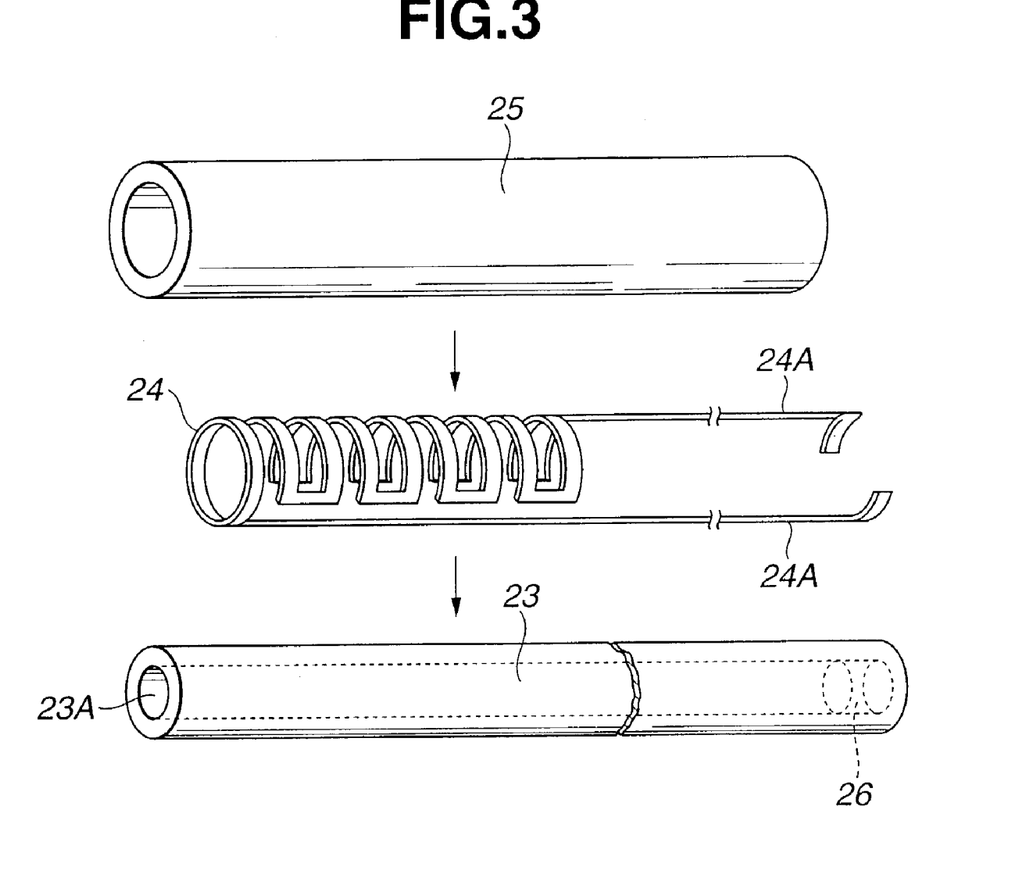
FIG. 3 is an exploded perspective view showing parts of a heater portion of the air/fuel ratio detection device.
Figure 4:
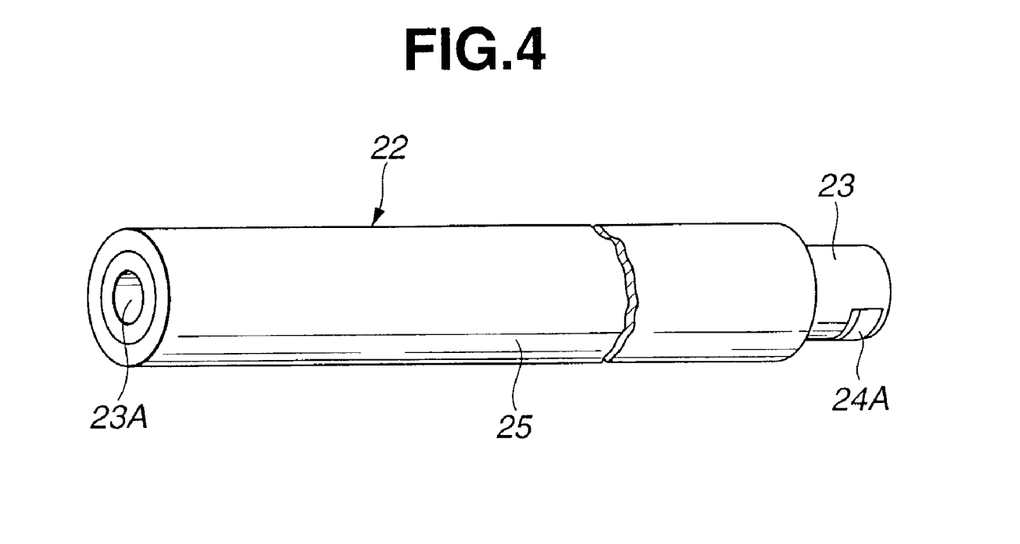
FIG. 4 is a perspective view showing the heater portion in which the parts of FIG. 3 have been assembled together.

As is seen from FIGS. 2–4, heater portion 22 (having an elongate cylindrical shape) comprises (a) core pipe 23 formed into a hollow cylindrical shape by a ceramic material (e.g., alumina), (b) heater pattern, and (c) insulating, heater covering layer 25.

As is seen from FIG. 3, heater pattern 24 is formed on the periphery of core pipe 23 by a curved surface printing or the like. Heater pattern 24 has a pair of leads 24A, 24A extending in the axial direction of core pipe 23. Heater covering layer 25 is formed on the periphery of core pipe 23 by a thick film printing using a ceramic material (e.g., alumina) for the purpose of protecting heater pattern 24 together with its leads 24*a*.

Core pipe 23 is formed into an elongate cylindrical shape by injection molding of a ceramic material (e.g., alumina), for example, to have a outer diameter of about 3–4 mm and an axial length of about 50–60 mm. Core pipe 23 has cylindrical hole 23A extending in the axial direction. This hole 23A reduces the volume of core pipe 23 and thereby serves to reduce heat capacity of core pipe 23. Core pipe 23 may be formed by extrusion besides the above-mentioned injection molding. Furthermore, core pipe 23 may have a solid structure as opposed to the above-mentioned hollow structure.

Heater pattern 24 is made of an exothermic conductive material (e.g., platinum mixed with 10 wt % of alumina). Each lead 24A is connected at the base end portion of core pipe 23 with each contact plate 14, as shown in FIG. 1. Electricity is supplied to heater pattern 24 from the after-mentioned power source 34 through leads 12, contact plates 14 and leads 24A, thereby heating heater portion 22 at a temperature of about 650–800° C.

Heater covering layer 25 is formed into a cylindrical, porous, insulating layer using a ceramic material (e.g., alumina). Solid electrolyte layer 27 and inner electrode 28 are laminated on the periphery of heater covering layer 25 by a curved surface printing or the like.

As is seen from FIG. 3, designated by numeral 26 is a plug. Similar to core pipe 23, plug 26 is made of a ceramic material (e.g., alumina). Plug 26 is fit into a base end of the cylindrical hole 23A to close the cylindrical hole 23A. Cylindrical hole 23A of core pipe 23 can be used as a centering hole for conducing a curved surface printing of the after-mentioned solid electrolyte layer 27, protecting layer 33, diffusion layer 34 and the like. Thus, it is preferable in the preparation of the air/fuel ratio sensor to carry out the sequential steps of (a) conducting a curved surface printing of solid electrolyte layer 27, protecting layer 33, diffusion layer 34 and the like; (b) forming plug 26 at the base end portion of cylindrical hole 23A; and (c) sintering plug 26 together with core pipe 23.

Figure 5:
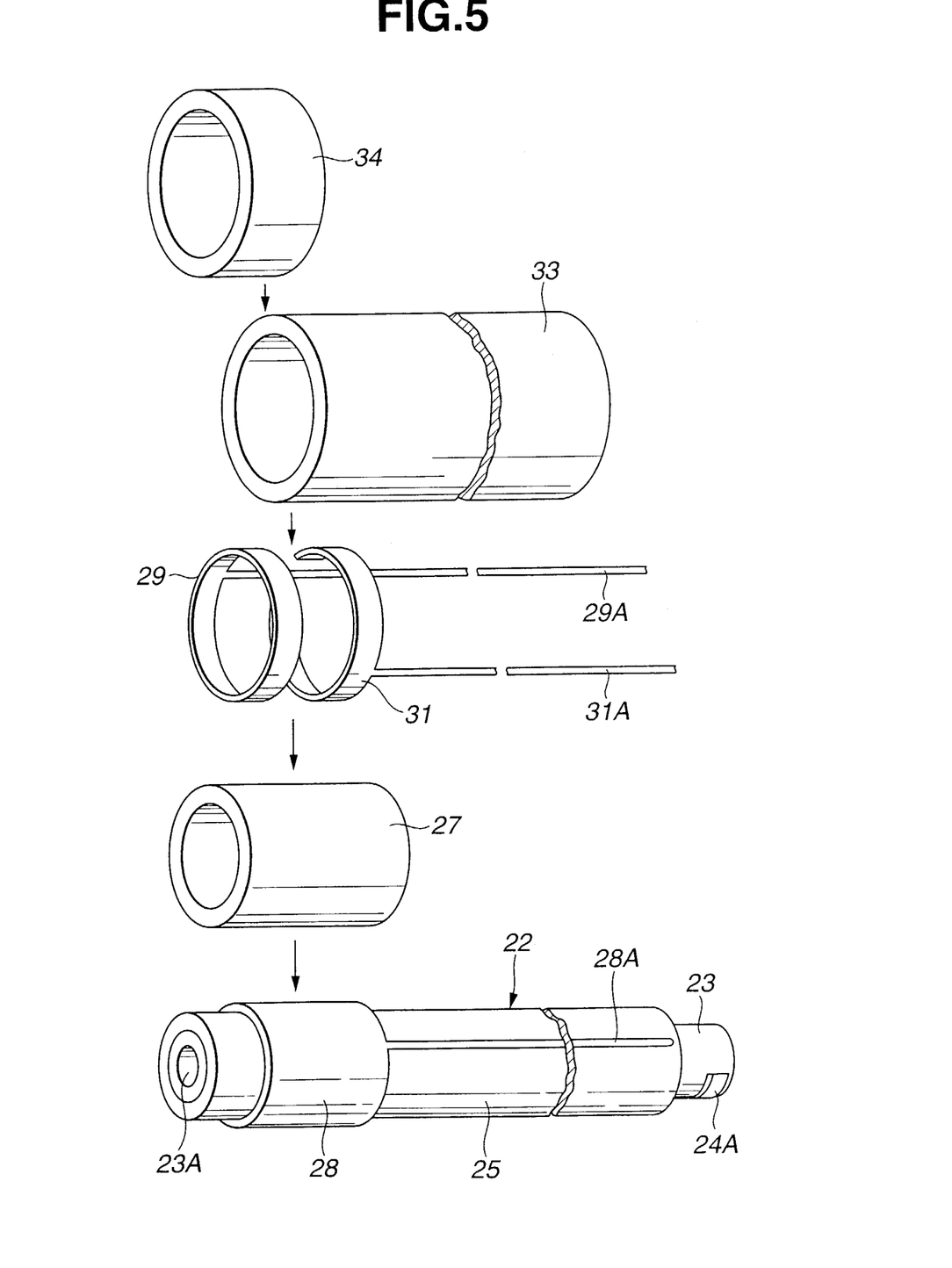
FIG. 5 is a perspective view showing further parts of the air/fuel ratio detection device.

As is seen from FIG. 2, designated by numeral 27 is an oxygen ion conductive solid electrolyte layer. Solid electrolyte layer 27 is formed on the periphery of heater covering layer 25 of heater portion 22 by using a curved surface printing technique or the like. As is shown in FIG. 5, solid electrolyte layer 27 can be formed into a cylindrical shape by conducting a thick film printing of a paste on the periphery of heater covering layer 25. This paste can be made from a mixture (a so-called yttria-stabilized zirconia (YSZ)) of 95 mol % of a zirconia ($ZrO_2$) powder and 5 mol % of an yttria ($Y_2O_3$) powder.

Solid electrolyte layer 27 has a thickness of, for example, about 50–100 μm and transports oxygen ions therethrough between electrodes 28, 29 and between electrodes 28, 31. With this, solid electrolyte layer 27 generates the after-mentioned Nernst voltages Vnl, Vnt, Vnr according to air-fuel ratio.

Designated by numeral 28 is an inner electrode (first electrode) that is positioned between heater covering layer 25 of heater portion 22 and solid electrolyte layer 27 and that is formed on the inner surface of solid electrolyte layer 27. As shown in FIG. 5, inner electrode 28 can be formed on the periphery of heater covering layer 25 (porous insulating layer) by conducting a curved surface printing, prior to curved surface printing of solid electrolyte layer 27.

Figure 7:
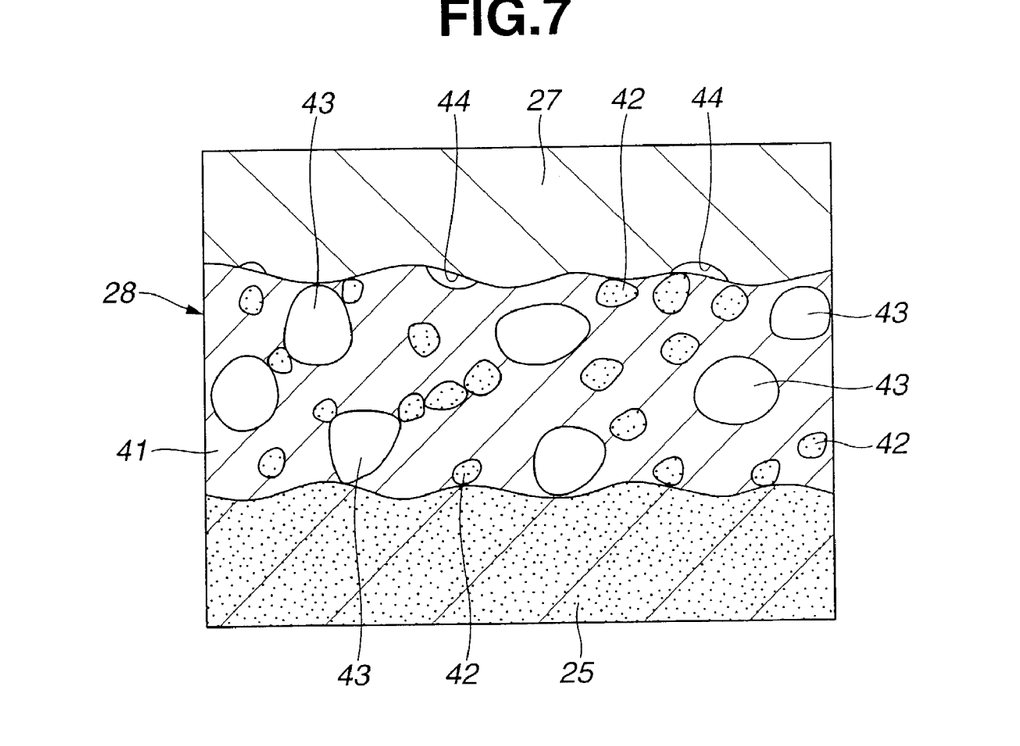
FIG. 7 is an enlarged, sectional, schematic view showing an inside structure of an inner electrode of the air/fuel ratio detection device.

As shown in FIG. 7, inner electrode 28 can be formed into a cylindrical electrode to have a predetermined length in the axial direction of heater covering layer 25 or solid electrolyte layer 27 by conducting a curved surface printing in which a paste containing the after-mentioned noble metal material 41 and ceramic grains 42 is applied to the periphery of heater covering layer 25.

As shown in FIG. 2, inner electrode 28 is opposed at its one side (leading end side) in the axial direction with the after-mentioned measuring electrode 29 in the radial direction of solid electrolyte layer 27 and is opposed at its the other side (base end side) in the axial direction with the after-mentioned reference electrode 31 in the radial direction of solid electrolyte layer 27.

Inner electrode 28 has a pair of leads 28A (only one is shown in FIG. 5A) extending toward the base end of heater portion 22 in the axial direction of heater covering layer 25. Solid electrolyte layer 27 is formed on the periphery of heater covering layer 25 by curved surface printing in a manner to fully surround inner electrode 28 from outside except its leads 28A.

Designated by numeral 29 is a measuring electrode (second electrode) that is formed on the periphery of solid electrolyte layer 27 at a position close to the leading end of heater portion 22. As shown in FIG. 2, measuring electrode 29 is at a position to interpose solid electrolyte layer 27 between measuring electrode 29 and inner electrode 28 and thereby constitutes measuring cell 30 as a first pumping cell.

Designated by numeral 31 is a reference electrode (third electrode) that is formed on the periphery of solid electrolyte layer 27 at a position away from measuring electrode 29 in the axial direction of heater portion 22. As shown in FIG. 2, reference electrode 31 is a position to interpose solid electrolyte layer 27 between reference electrode 31 and inner electrode 28 and thereby constitutes reference cell 32 as a second pumping cell.

Measuring electrode 29 and reference electrode 31 can be formed on the periphery of solid electrolyte layer 27 by conducting a curved surface printing using a conductive paste of platinum or the like to have a printing pattern shown in FIG. 5. Their leads 28A, 31A extend toward the base end of heater portion 22.

Each lead 28A of inner electrode 28, lead 29A of measuring electrode 29 and lead 31A of reference electrode 31 are connected at the base end side of air/fuel ratio detection device 21 with corresponding contact plate 13 and lead 11. As shown in FIG. 2, working voltage Va (first voltage) is applied between inner electrode 28 and measuring electrode 29 from the after-mentioned direct current power source 36.

Working voltage Vb (second voltage) is applied between inner electrode 28 and reference electrode 31 from the after-mentioned direct current power source 39. On the side of reference cell 32, reference electrode 31 becomes a cathode for conducting reactions shown in the after-mentioned reaction formulas (1) and (3), and inner electrode 28 becomes an anode. With this, oxygen is attracted from reference electrode 31 toward inner electrode 28, as mentioned hereinafter.

On the other hand, on the side of measuring cell 30, under a lean air/fuel ratio condition ($\lambda > 1$), reference electrode 29 becomes cathode for conducting the reaction shown in reaction formula (1), and inner electrode 28 becomes anode to attract oxygen. In contrast, under a rich air/fuel ratio condition ($\lambda < 1$), reference electrode 31 turns into anode, and inner electrode 28 serves as cathode.

Designated by numeral 33 is a protecting layer for covering a part of solid electrolyte layer 27 as well as reference electrode 31. As shown in FIGS. 2 and 5, protecting layer 33 is formed into a cylindrical body to have a thickness of, for example, about 30–100 μm by a paste of alumina powder and magnesium oxide (MgO) powder and then by applying the paste to the peripheries of solid electrolyte layer 27 and heater covering layer 25 using a curved surface printing.

The thus formed protecting layer 33 is made to have a porous structure having a porosity higher than that of the after-mentioned diffusion layer 34. Protecting layer 33 covers solid electrolyte layer 27 from outside except its leading end portion having thereon measuring electrode 29.

Protecting layer 33 has a function of protecting heater covering layer 25, solid electrolyte layer 27 and reference electrode 31. A part of the exhaust gas flowing around protecting layer 33 is allowed to pass through protecting layer 33 (having a high porosity) toward reference electrode 31.

Designated by numeral 34 is a diffusion layer made of a porous material for covering solid electrolyte layer 27 and measuring electrode 29 from outside. For example, as shown in FIGS. 2 and 5, diffusion layer 34 can be formed into a cylindrical body to have a thickness of, for example, about 30–100 μm by applying a paste of alumina powder to the periphery of the leading end portion of solid electrolyte layer 27. It is optional to add a predetermined amount of zirconia powder to the alumina powder paste in the preparation of diffusion layer 34.

Diffusion layer 34 is formed to have a porous structure having finer pores as compared with those of protecting layer 33 and thereby has a function to allow a part of the exhaust gas flowing around diffusion layer 34 to pass through diffusion layer 34 toward measuring electrode 29. Transmission of the exhaust gas (gas diffusion resistance) can be adjusted by changing the thickness of diffusion layer 34. As shown in FIG. 2, diffusion layer 34 is positioned to cover the leading end side of heater portion 22. Therefore, it is easily possible to adjust thickness of diffusion layer 34 from outside following the removal of protector 15.

In fact, it is possible to suitably adjust transmission (gas diffusion resistance) of the exhaust gas, for example, by grinding the periphery of diffusion layer 34 using a diamond grinding. Furthermore, diffusion layer 34 can be formed by plasma spraying to cover the periphery of the leading end side of solid electrolyte layer 27 using a porous ceramic material, for example, of alumina.

Designated by numeral 35 is a heater power source provided outside of casing 1. As is shown in FIG. 2, heater power source 35 is connected with heater pattern 24 through lead 12 and the like. Heater power source 35 heats heater portion 22 at a temperature of about 650–800° C. by applying voltage to heater pattern 24 of heater portion 22.

Designated by numeral 36 is a direct current power source (first voltage applying device) provided outside of casing 1. As is shown in FIG. 2, direct current power source 36 is connected with inner electrode 28 and measuring electrode 29 through lead 11, thereby applying working voltage Va (first voltage) between electrodes 28, 29. Working voltage Va of direct current power source 36 may be kept at a constant voltage (e.g., about 450 mV) or varied according to need.

Designated by numeral 37 is an ammeter disposed between and connected with direct current power source 36 and measuring electrode 29. Ammeter 37 detects diffusion limiting current Im (outputted from measuring electrode 29) corresponding to air/fuel ratio, as shown by characteristic line 38 of FIG. 8.

Designated by numeral 39 is a direct current power source (second voltage applying device) provided outside of casing 1. As is shown in FIG. 2, direct current power source 39 is connected with inner electrode 28 and reference electrode 31 through lead 11, thereby applying working voltage Vb (second voltage) between electrodes 28, 31. In this case, working voltage Vb of direct current power source 39 is kept at a constant voltage (e.g., about 1.6V). This working voltage Vb becomes higher than working voltage Va of direct current power source 36, and may be adjusted according to need.

Working voltage Va of direct current power source 36 and working voltage Vb of direct current power source 39 are adjusted in advance such that the amount of oxygen absorbed into void spaces 43 (oxygen receiving chambers) of inner electrode 28 due to the after-mentioned combined pumping voltage Upb is larger than the amount of oxygen absorbed out of void spaces 43 of inner electrode 28 due to the after-mentioned pumping voltage Upa. Upon this, working voltages Va and Vb are adjusted to satisfy the expression (7).

Figure 8:
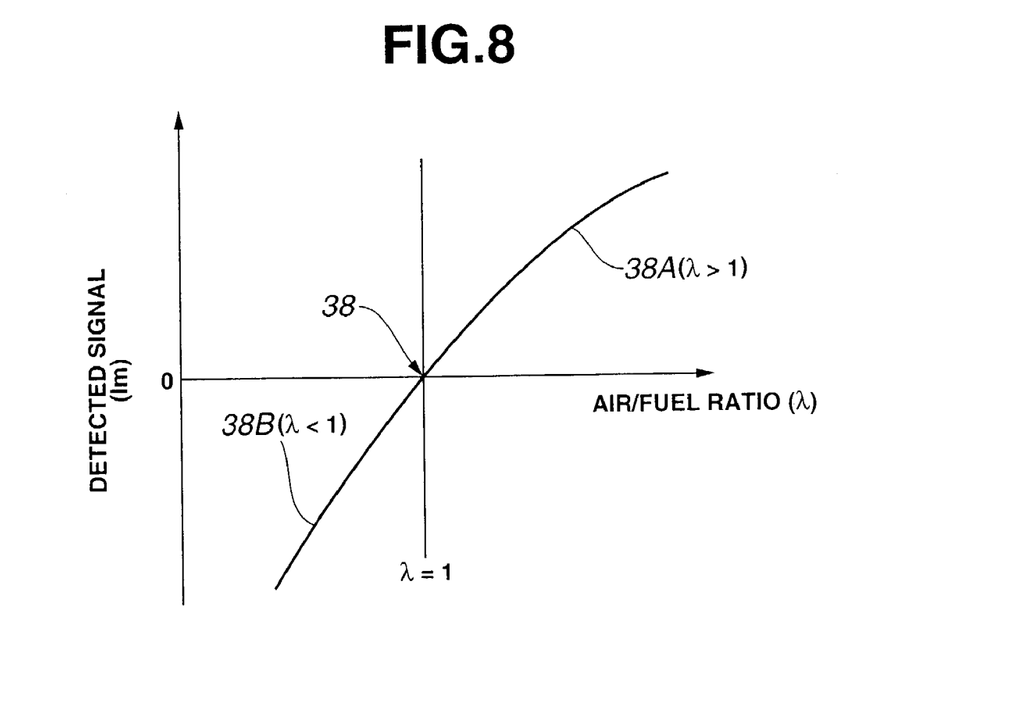
FIG. 8 is a characteristic diagram showing a relationship between air/fuel ratio ($\lambda$) and the detected signal (Im) from the air/fuel ratio detection device.

By adjusting working voltage Va of direct current power source 36 and working voltage Vb of direct current power source 39, the signal outputted as diffusion limiting current Im from measuring electrode 29 is detected by ammeter 37 as the detected signal that changes according to air/fuel ratio, as shown by characteristic line 38 of FIG. 8.

The structure of inner electrode 28 will be explained in the following with reference to FIG. 7. Inner electrode 28 is formed of noble metal material 41 (e.g., platinum), ceramic grains 42, and void spaces 43. For example, ceramic grains 42 can be prepared by mixing a zirconia powder having a grain size of about 0.4–1.0 μm with an alumina powder having a grain size of about 0.4–1.0 μm.

Void spaces 43 can be formed by using a void space forming agent containing a carbon powder having a grain size of about 0.4–3.0 μm. This void space forming agent is vaporized upon baking of air/fuel ratio detecting device 21, thereby forming in inner electrode 28 void spaces 43 that are continuous bubbles. Void spaces 43 have a size comparable to or greater than that of ceramic grains 42. With this, it is possible to increase the amount of oxygen to be received in the void spaces, thereby smoothly conducting diffusion of oxygen in inner electrode 28.

Inner electrode 28 can be prepared by mixing a powder of noble metal material 41 with, for example, 15–20 wt % of zirconia powder, 1–2 wt % of alumina powder and 1–5 wt % of carbon powder to prepare a paste and then by applying the paste to the periphery of heater covering layer 25. In this case, it is optional to replace the alumina powder with 1–2 wt % of mullite ($3Al_2O_3 \cdot 2SiO_2$) powder.

Inner electrode 28 serves to transport electrons therein since noble metal material generates an electrode reaction. Inner electrode 28 is improved in adhesion to heater covering layer 25 (porous insulating layer) and solid electrolyte layer 27 by containing a zirconia powder and an alumina or mullite powder in ceramic grains 42.

As mentioned above, void spaces (continuous bubbles) 43 formed in inner electrode 28 serve as oxygen receiving chambers in inner electrode 28. As shown in FIGS. 5–6, lead 28A of inner electrode 28 also contain void spaces 43. With this, the oxygen receiving chambers of void spaces 43 are in communication with the atmosphere in casing 1 (particularly cap 3), as shown in FIG. 1.

The existence of void spaces 43 of inner electrode 28 increases the number of three-phase interfaces (serving as electrode reaction points) formed among solid electrolyte layer 27, noble metal material 41 and void spaces 43. Since void spaces 43 serve as oxygen receiving chambers, they serve to diffuse oxygen throughout inner electrode 28 in accordance with its concentration gradient and pressure gradient. As shown in FIG. 7, there may exist recesses 44 in the vicinity of the boundary between solid electrolyte layer 27 and inner electrode 28 to form three-phase interfaces formed among recesses 44, solid electrolyte layer 27 and noble metal material 41.

With reference to FIGS. 3 to 6, the method for producing air/fuel ratio detection device 21 will be explained in the following.

For producing heater portion 22, a ceramic material (e.g., alumina) is formed into a hollow cylindrical rod as core pipe 23 by injection molding, followed by preliminary sintering. In this case, it is preferable to enlarge the diameter of cylindrical hole 23A as large as possible in order to reduce heat capacity of core pipe 23.

In the pattern-printing step, a supporting shaft (e.g., chuck) is engaged with both ends of cylindrical hole 23 to rotate core pipe 23. While core pipe 23 is rotated, an exothermic conductive material (e.g., platinum mixed with 10 wt % alumina) is applied to the periphery of core pipe 23 by curved surface printing to form heater pattern 24. Furthermore, each lead 24A of heater pattern 24 is printed to extend toward the base end of core pipe 23, thereby making heater pattern have a one-piece construction.

Then, heater covering layer 25 for covering heater pattern 24 is formed by conducting a curved surface printing using a paste (e.g., alumina) or by putting a ceramic green sheet (e.g., of alumina) on the outside of core pipe 23. With this, there is provided heater portion 22 formed of core pipe 23, heater pattern 24 and heater covering layer 25, as shown in FIG. 4.

Then, as shown in FIG. 5, inner electrode 28 (cylindrical electrode) is formed by conducting a curved surface printing of a paste (containing the above-mentioned noble metal material 41, ceramic grains 42 and the like) on the periphery of heater covering layer 25. Furthermore, leads 28A of inner electrode 28 are formed by printing such that these leads extend toward the base end of heater covering layer 25 while they are away from each other.

Oxygen ion conductive solid electrolyte layer 27 is formed by conducting a curved surface printing of a paste (e.g., containing a mixture of zirconia and yttria) on the periphery of heater covering layer 25 in a manner to cover inner electrode 28.

Then, measuring electrode 29 and reference electrode 31 are formed by conducting a curved surface printing of a conductive paste (e.g., of platinum) on the peripheral surface of solid electrolyte layer 27 such that these electrodes are away from each other along the axial direction of solid electrolyte layer 27. Furthermore, leads 29A and 31A are formed by printing such that these leads extend toward the base end of heater covering layer 25 while they are away from each other.

Then, as shown in FIG. 5, protecting layer 33 is formed by conducting a curved surface printing of a paste (e.g., of alumina and magnesium oxide) on the peripheries of solid electrolyte layer 27 and heater portion 22 to cover reference electrode 31.

Diffusion layer 34 is formed by conducting a curved surface printing of a paste (e.g., of alumina or of an alumina containing zirconia) on the periphery of the leading end side of solid electrolyte layer 27 to cover measuring electrode 29.

Then, an assembly of core pipe 23, heater pattern 24, heater covering layer 25, solid electrolyte layer 27, electrodes 28, 29 and 31, protecting layer 33, and diffusion layer 34 is subjected to a sintering for about 2 hr at a high temperature, for example, of about 1,300–1,500° C. With this, the sintered assembly is made to have a one-piece construction. Furthermore, it is preferable to form plug 26 (shown in FIG. 3) in cylindrical hole 23A of core pipe 23 prior to sintering, and then to conduct its sintering together with the above-mentioned members.

As is shown in FIG. 1, the thus produced air/fuel ratio detection device 21 is put into casing 1 in a manner to bring leads 24A, 28A, 29A and 31A into contact with respective contact plates 13, 14, thereby completing air/fuel ratio sensor.

Operation of air/fuel detection sensor will be described as follows. Casing 1 is threadedly secured to a vehicular exhaust pipe through external threaded portion 2A such that a leading end portion of air/fuel ratio detection device 21 protrudes into the inside space of the exhaust pipe.

Then, an exhaust gas flowing through the exhaust pipe reaches surroundings of air/fuel ratio detection device 21 through protector 15 by starting engine, and a part of this exhaust gas is transmitted through protecting layer 33 and diffusion layer 34 and then reaches the surfaces of reference electrode 31 and measuring electrode 29.

Air/fuel ratio detection device 21 is heated by heater portion 22 as electricity is supplied from heater power source 35 to heater pattern 24. With this, solid electrolyte layer 27 is activated. Thereby, working voltage Va (e.g., 450 mV) is applied by direct current power source 36 between inner electrode 28 and measuring electrode 29, which are opposed to each other with an interposal of solid electrolyte layer 27. Furthermore, working voltage Vb (e.g., 1.6V) is applied by direct current power source 39 between inner electrode 28 and reference electrode 31.

By working voltages Va and Vb, Nernst voltages Vnl, Vnt and Vnr are generated between inner electrode 28 and reference electrode 31 of reference cell 32 and between inner electrode 28 and measuring electrode 29 of measuring cell 30 according to the oxygen concentration and combustible gas component concentration. The resulting diffusion limiting current Im is outputted as a detected signal by ammeter 37 to determine air/fuel ratio ($\lambda$) by the relationship between the detected signal and air/fuel ratio ($\lambda$) shown in FIG. 8. Details for determining air/fuel ratio ($\lambda$) are explained in the following.

At first, there will be discussed the case of lean air/fuel ratio ($\lambda$>1) in which air/fuel ratio of engine is greater than stoichiometric air/fuel ratio ($\lambda$=1). In this case, unburned oxygen remains in the exhaust gas flowing around protecting layer 33 and diffusion layer 34 after combustion of a lean fuel-air mixture in combustion chamber.

Therefore, in a condition in which working voltage Vb (actually the after-mentioned combined pumping voltage Upb) is applied between inner electrode 28 and reference electrode 31 of reference cell 32, a reaction represented by the following reaction formula (1) proceeds at reference electrode (cathode) 31. In fact, electrons are added to molecular oxygen remaining in the exhaust gas to generate oxygen ions.

$$O_2 + 4e(\text{electron}) \rightarrow 2O^{2-} \qquad (1)$$

The resulting oxygen ions are transported from reference electrode (cathode) 31 toward inner electrode (anode) 28 by passing through oxygen defects in solid electrolyte layer 27.

The oxygen ions are decomposed at inner electrode (anode) 28 into oxygen ions and electrons, as shown in the following reaction formula (2).

$$2O^{2-} \rightarrow O_2 + 4e(\text{electron}) \quad (2)$$

Figure 9:
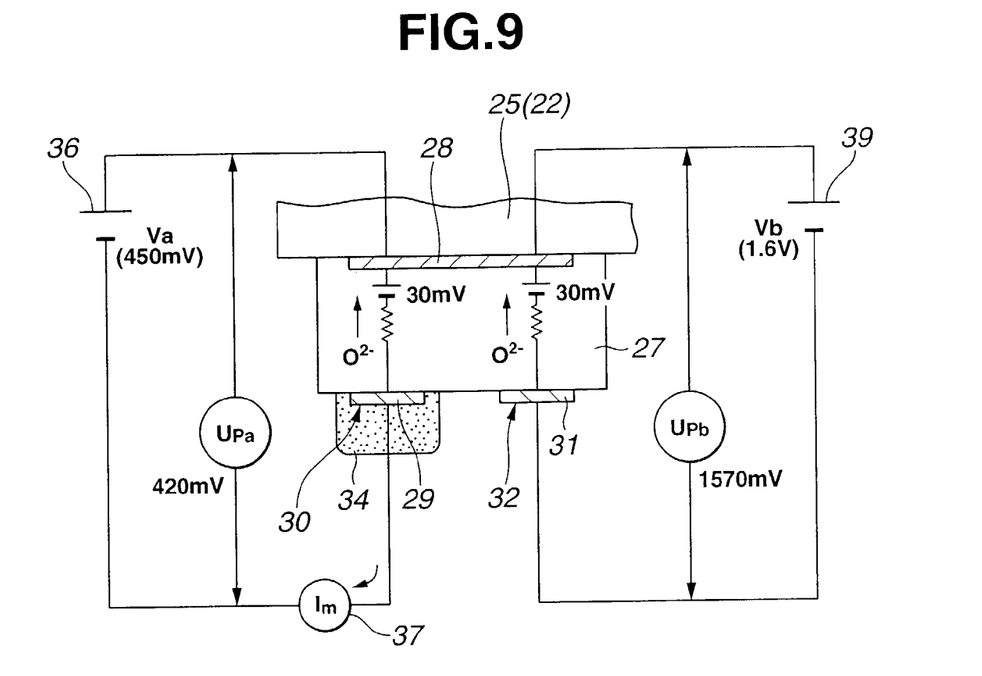
FIG. 9 is a schematic diagram showing the process for detecting air/fuel ratio under a lean air/fuel ratio condition.
Figure 10:
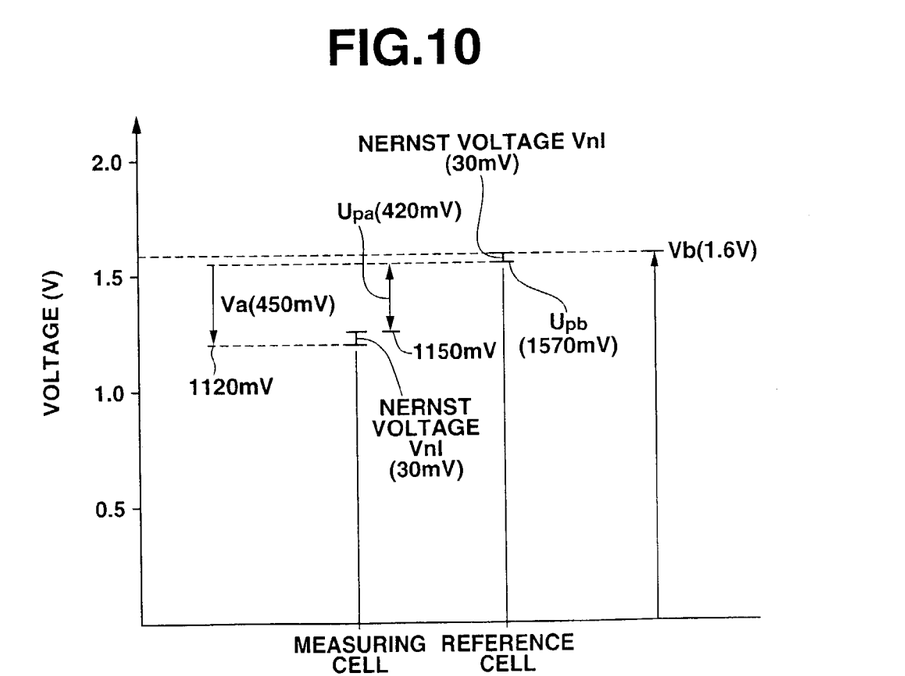
FIG. 10 is a characteristic diagram showing voltages of the reference and measuring cells under a lean air/fuel ratio condition.

In inner electrode 28, the resulting molecular oxygen is absorbed into void spaces 43 shown in FIG. 7, thereby generating in void spaces an oxygen partial pressure higher than that of reference electrode 31 or that of external exhaust gas. Upon this, as shown in FIGS. 9 and 10, Nernst voltage Vnl (e.g., about 30 mV) is generated according to the oxygen partial pressure difference between electrodes 28, 31 under a lean air/fuel ratio condition.

The above Nernst voltage Vnl acts in a direction opposite to working voltage Vb (e.g., 1.6V) of direct current power source 39. Consequently, combined pumping voltage Upb (e.g., 1570 mV) is applied between electrodes 28, 31 of reference cell 32, as shown in the following expression (1).

$$Upb = Vb - Vnl = 1600 - 30 = 1570 \quad (1)$$

The above Nernst voltage Vnl (e.g., about 30 mV) also acts in the opposite direction between electrodes 28, 29 of measuring cell 30. Consequently, pumping voltage Upa (e.g., 420 mV) is applied between electrodes 28, 29 of measuring cell 30, as shown in the following expression (2).

$$Upa = Va - Vnl = 450 - 30 = 420 \quad (2)$$

The above-mentioned electrochemical reaction represented by the reaction formula (1) also occurs at measuring electrode (cathode) 29 of measuring cell 30. In fact, electrons are added to oxygen remaining in the exhaust gas to generate oxygen ions. The resulting oxygen ions are decomposed into oxygen and electrons at inner electrode (anode) 28, as shown in the reaction formula (2).

The resulting oxygen is absorbed in inner electrode (anode) 28, and thereby diffusion limiting current Im is allowed to flow from reference electrode 29 toward ammeter 37, as shown in FIG. 9. Ammeter detects and outputs this diffusion limiting current Im as a detected signal to determine lean air/fuel ratio using the characteristic line of FIG. 8.

Figure 11:
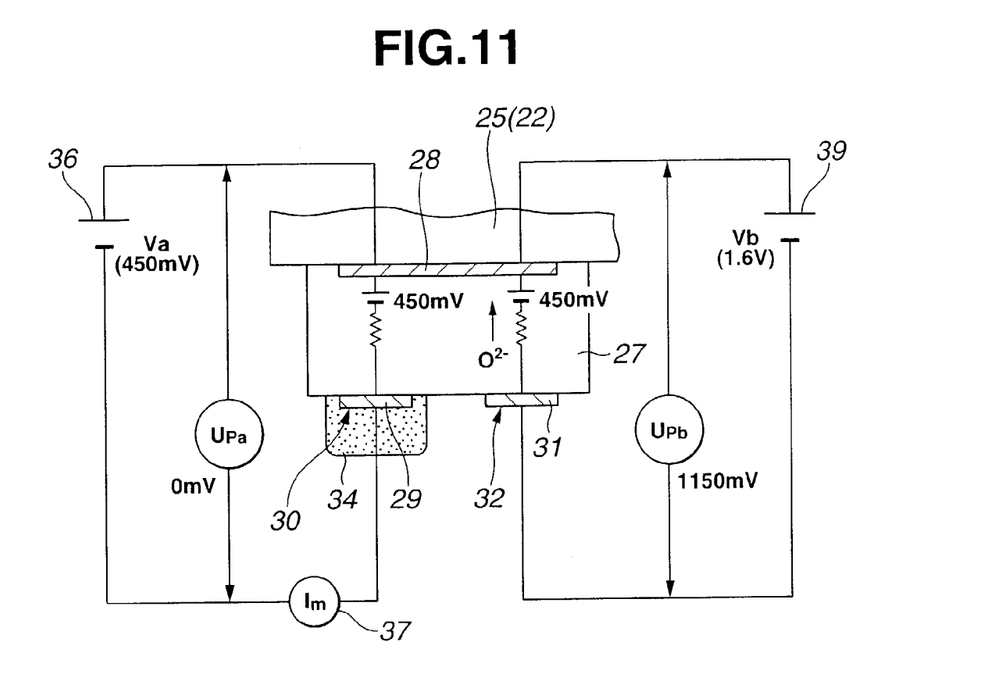
FIG. 11 is a schematic diagram showing the process for detecting air/fuel ratio under stoichiometric air/fuel ratio condition.
Figure 12:
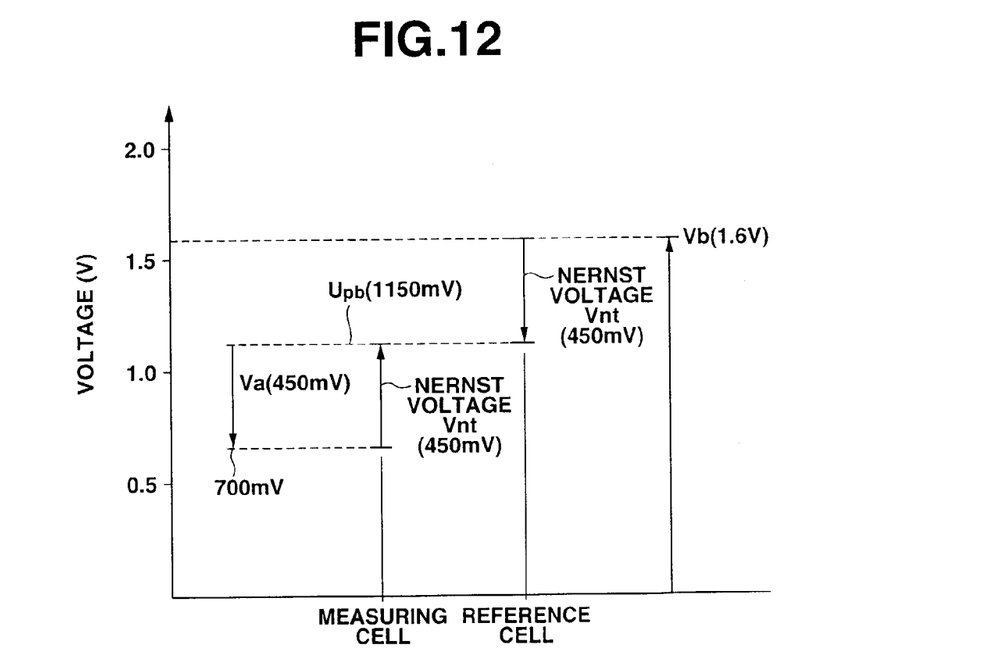
FIG. 12 is a characteristic diagram showing voltages of the reference and measuring cells under stoichiometric air/fuel ratio condition.

Next, there will be discussed the case in which air/fuel ratio of engine is stoichiometric air/fuel ratio ($\lambda$=1). In this case, as shown in FIGS. 11 and 12, Nernst voltage Vnt (e.g., about 450 mV) is generated according to the oxygen partial pressure difference between electrodes 28, 31 and between electrodes 28, 29.

The above Nernst voltage Vnt acts in a direction opposite to working voltage Vb (e.g., 1.6V) of direct current power source 39. Consequently, combined pumping voltage Upb (e.g., 1150 mV) is applied between electrodes 28, 31 of reference cell 32, as shown in the following expression (3).

$$Upb = Vb - Vnt = 1600 - 450 = 1150 \quad (3)$$

Similar to the case of lean air/fuel ratio ($\lambda$>1), oxygen ions are also generated at reference electrode 31 by the addition of electrons to oxygen remaining in the exhaust gas in the case of stoichiometric air/fuel ratio, as shown in the reaction formula (1). The resulting oxygen ions are transported from reference electrode 31 to inner electrode 28 by passing through oxygen defects of solid electrolyte layer 27. Then, the oxygen ions are decomposed into oxygen and electrons in inner electrode 28, as shown in the reaction formula (2). The resulting oxygen is absorbed into void spaces 43 (shown in FIG. 7), thereby generating a higher oxygen partial pressure in void spaces 43 than that of reference electrode 31. Due to this oxygen partial pressure difference, the above-mentioned Nernst voltage Vnt (e.g., about 450 mV) under stoichiometric air/fuel ratio condition is generated continuously between electrodes 28, 31.

The above Nernst voltage Vnt also acts in the opposite direction between electrodes 28, 29 of measuring cell 30. Consequently, pumping voltage Upa applied between electrodes 28, 29 of measuring cell 30 is suppressed to 0V, as shown in the following expression (4).

$$Upa = Va - Vnt = 450 - 450 = 0 \quad (4)$$

Thus, diffusion limiting current Im does not flow from reference electrode 29 toward ammeter 37, as shown in FIG. 11. Ammeter detects and outputs this diffusion limiting current Im (0V) as a detected signal. With this, air/fuel ratio ($\lambda$) is judged as being one (1).

Next, there will be discussed the case of rich air/fuel ratio ($\lambda$<1) in which air/fuel ratio of engine is less than stoichiometric air/fuel ratio ($\lambda$=1). In this case, oxygen does not remain in the exhaust gas flowing around protecting layer 33 and diffusion layer 34 after combustion of a rich fuel-air mixture in combustion chamber. In contrast, unburned combustible gas components (e.g., carbon monoxide (CO) and hydrogen ($H_2$)) remain in the exhaust gas.

Therefore, in a condition in which working voltage Vb (actually the after-mentioned combined pumping voltage Upb) of direct current power source 39 is applied between inner electrode 28 and reference electrode 31 of reference cell 32, electrons are added, for example, to carbon dioxide remaining in the exhaust gas, thereby generating oxygen ions and carbon monoxide, as shown in the following reaction formula (3).

$$2CO_2 + 4e(\text{electrons}) \rightarrow 2O^{2-} + 2CO \quad (3)$$

Similar to the case of lean air/fuel ratio condition, the resulting oxygen ions are transported from reference electrode (cathode) 31 toward inner electrode (anode) 28 by passing through oxygen defects in solid electrolyte layer 27. The oxygen ions are decomposed at inner electrode (anode) 28 into oxygen ions and electrons, as shown in reaction formula (2).

Figure 13:
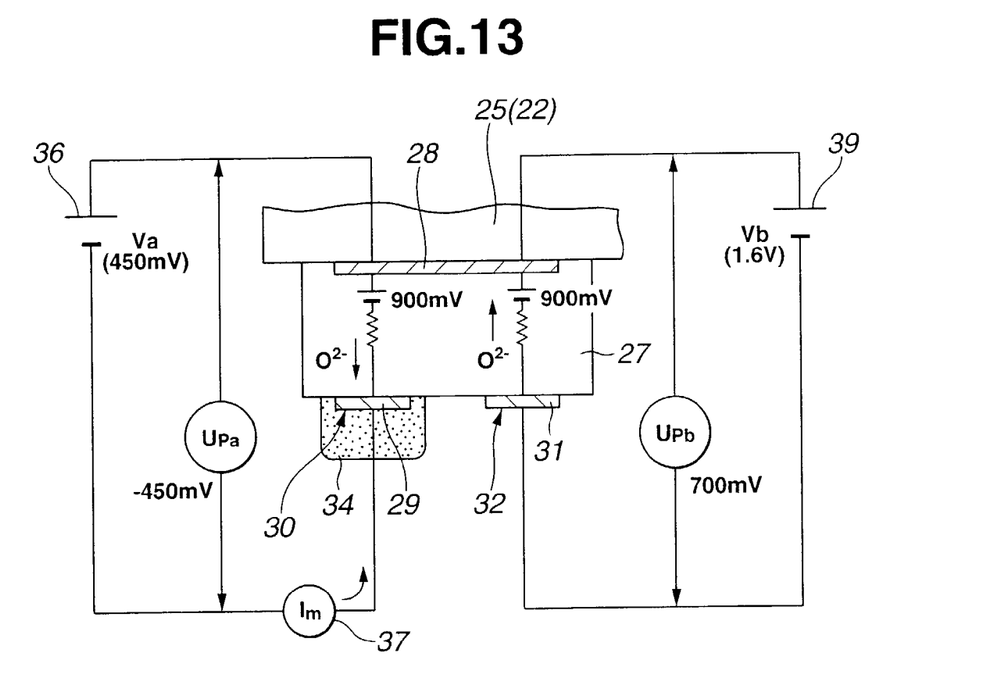
FIG. 13 is a schematic diagram showing the process for detecting air/fuel ratio under a rich air/fuel ratio condition.
Figure 14:
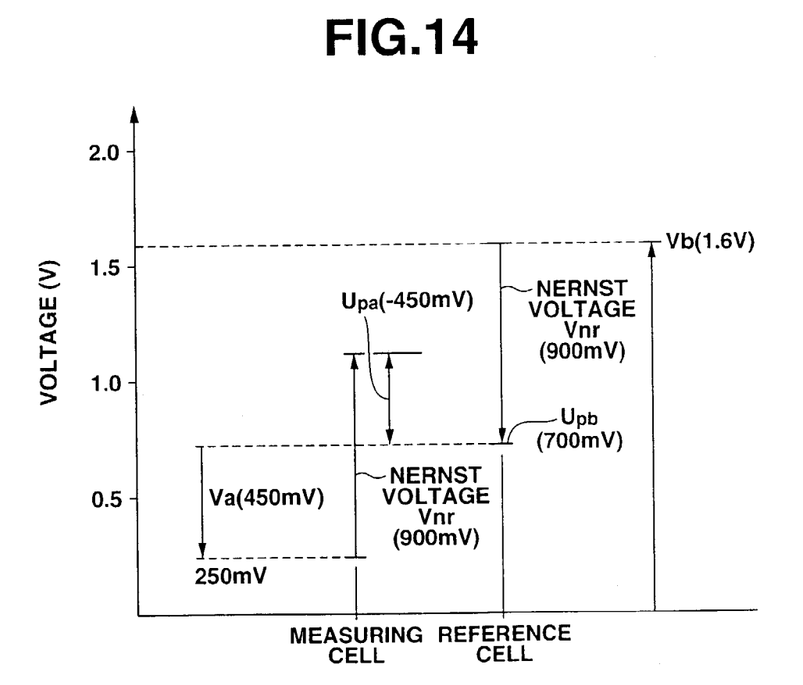
FIG. 14 is a characteristic diagram showing voltages of the reference and measuring cells under a rich air/fuel ratio condition.

In inner electrode 28, the resulting molecular oxygen is absorbed into void spaces 43 shown in FIG. 7, thereby generating in void spaces an oxygen partial pressure higher than that of reference electrode 31 or that of external exhaust gas. Upon this, as shown in FIGS. 13 and 14, Nernst voltage Vnr (e.g., about 900 mV) is generated according to the oxygen partial pressure difference between electrodes 28, 31 under a rich air/fuel ratio condition.

The above Nernst voltage Vnr acts in a direction opposite to working voltage Vb (e.g., 1.6V) of direct current power source 39. Consequently, combined pumping voltage Upb (e.g., 700 mV) is applied between electrodes 28, 31 of reference cell 32, as shown in the following expression (5).

$$Upb = Vb - Vnr = 1600 - 900 = 700 \quad (5)$$

The above Nernst voltage Vnr (e.g., about 900 mV) also acts in the opposite direction between electrodes 28, 29 of measuring cell 30. Consequently, pumping voltage Upa (e.g., −450 mV) is applied between electrodes 28, 29 of measuring cell 30, as shown in the following expression (6).

$$Upa = Va - Vnr = 450 - 900 = -450 \quad (6)$$

Consequently, in the case of rich air/fuel ratio ($\lambda$<1), inner electrode 28 and measuring electrode 29 switch to cathode and anode, respectively. At inner electrode (cathode) 28, electrons are added to oxygen in void spaces 43 to generate oxygen ions, as shown in the reaction formula (1). At measuring electrode (anode) 29, the oxygen ions from inner electrode 28 are reacted, for example, with carbon monoxide, as shown in the following reaction formula (4)

$$2CO + 2O^{2-} \rightarrow 2CO_2 + 4e(electron) \quad (4)$$

In case that the combustible gas component in the exhaust gas is hydrogen ($H_2$), electrons are added to water molecule remaining in the exhaust gas, thereby generating oxygen ions and hydrogen, as shown in the following reaction formula (5).

$$2H_2O + 4e(electron) \rightarrow 2O^{2-} + 2H_2 \quad (5)$$

The resulting oxygen ions are transported from reference electrode (cathode) 31 toward inner electrode (anode) 28 by passing through oxygen defects in solid electrolyte layer 27. The oxygen ions are decomposed at inner electrode (anode) 28 into oxygen ions and electrons, as shown in reaction formula (2).

As stated above, inner electrode 28 and measuring electrode 29 switch by Nernst voltage to cathode and anode respectively in the case of rich air/fuel ratio ($\lambda<1$). At inner electrode (cathode) 28, electrons are added to oxygen in void spaces 43 to generate oxygen ions, as shown in the reaction formula (1).

At measuring electrode (anode) 29, the oxygen ions from inner electrode 28 are reacted with hydrogen to generate water molecules and electrons, as shown in the following reaction formula (6)

$$2H_2 + 2O^{2-} \rightarrow 2H_2O + 4e(electrons) \quad (6)$$

Therefore, diffusion limiting current Im is allowed to flow from measuring electrode 29 toward inner electrode 28, as shown by the arrow of FIG. 13. Ammeter detects and outputs this diffusion limiting current Im as a detected signal to determine lean air/fuel ratio using the characteristic line of FIG. 8.

In this case, Nernst voltage Vnr (e.g., about 900 mV) under rich air/fuel ratio condition is set, relative to working voltage Va (e.g., 450 mV) of direct current power source 36 and working voltage (e.g., 1.6V) of direct current power source 39, in a manner to satisfy the following expression (7).

$$2 \times Vnr < (Va + Vb) \quad (7)$$

As stated above, combined pumping voltage Upb of reference cell 32 is higher than pumping voltage Upa of measuring cell 30 in the case of rich air/fuel ratio, too. Therefore, the amount of oxygen absorbed by combined pumping voltage Upb into void spaces (oxygen receiving chambers) 43 of inner electrode 28 is set to be higher than that of oxygen absorbed by pumping voltage Upa out of void spaces 43 of inner electrode 28.

Thus, oxygen partial pressure of void spaces 43 of inner electrode 28 is always kept higher than the external exhaust gas. As shown in FIGS. 5–6, lead 28A of inner electrode 28 also contain void spaces 43. With this, as shown in FIG. 1, the oxygen receiving chambers of void spaces 43 are in communication with the atmosphere in casing 1, thereby preventing a so-called reverse diffusion of the external exhaust gas toward void spaces 43.

According to the above-mentioned embodiment of the present invention, it is possible to output diffusion limiting current Im (as a detected signal) that changes according to air/fuel ratio, as shown by the characteristic line of FIG. 8. Specifically, it is possible to output a detected signal of zero current value when it is stoichiometric air/fuel ratio ($\lambda=1$), that of a positive current value when it is lean air/fuel ratio ($\lambda>1$), and that of a negative current value when it is rich air/fuel ratio ($\lambda<1$).

As stated above, it is possible to produce air/fuel ratio detecting device 21 into a cylindrical shape in its entirety. Therefore, it is possible to provide electrodes 28, 29, 31 with sufficient electrode areas and to reduce internal resistance and size of air/fuel ratio detecting device 21, as compared with conventional air/fuel ratio detecting devices of platy shape.

Furthermore, conventional air/fuel ratio detecting devices have edge portions due to their platy shape. In contrast, air/fuel ratio detecting device 21 of the present invention does not have such edge portions due to its cylindrical shape. Therefore, it is possible by air/fuel ratio detecting device 21 to reduce thermal stress and the like by about a half. This makes it possible to prevent, for example, cracks of solid electrolyte layer 27.

As stated above, heater portion 22 is fully covered with solid electrolyte layer 27, diffusion layer 34 and the like. With this, heater portion 22 is prevented from a direct contact with the outside air. Therefore, it is possible to efficiently transmit heat from heater portion to solid electrolyte layer 27 and the like.

Air/fuel ratio detecting device 21 has a construction in which solid electrolyte layer 27 is interposed between inner electrode 28 and measuring electrode 29 and between inner electrode 28 and reference electrode 31. With this, it is possible to form measuring cell 30 and reference cell 32 (first and second pumping cells) by using only a single layer of solid electrolyte layer 27.

It is possible to strongly bond inner electrode 28 to heater covering layer 25 and solid electrolyte layer 27 after sintering by using the same material for ceramic grains 42, heater covering layer 25 and solid electrolyte layer 27. Furthermore, it is possible to uniformly distribute many of the above-mentioned three-phase interfaces (electrode reaction points). Therefore, it is possible to generate the electrode reaction uniformly at the entirety of a first interface (between solid electrolyte layer 27 and inner electrode 28) opposed to measuring electrode 29 and at the entirety of a second interface (between solid electrolyte layer 27 and inner electrode 28) opposed to reference electrode 31.

It is possible to diffuse oxygen in void spaces 43. Therefore, it is possible to reduce the concentration and pressure differences of oxygen caused by the electrode reaction and the temperature change, thereby preventing accumulation and deficiency of oxygen at the three-phase interfaces. With this, it is possible to lower internal resistance of the sensor and to accelerate activation of air/fuel ratio detecting device 21 at low temperature.

Figure 15:
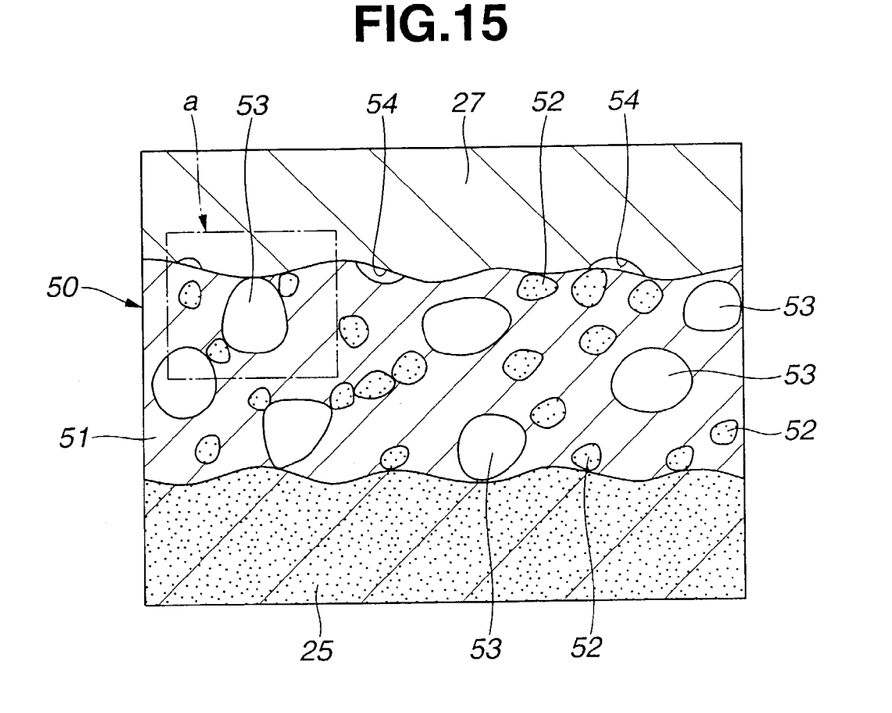
FIG. 15 is a view similar to FIG. 7, but showing an inside structure of an inner electrode of an air/fuel ratio detection device according to a second embodiment of the present invention.
Figure 16:
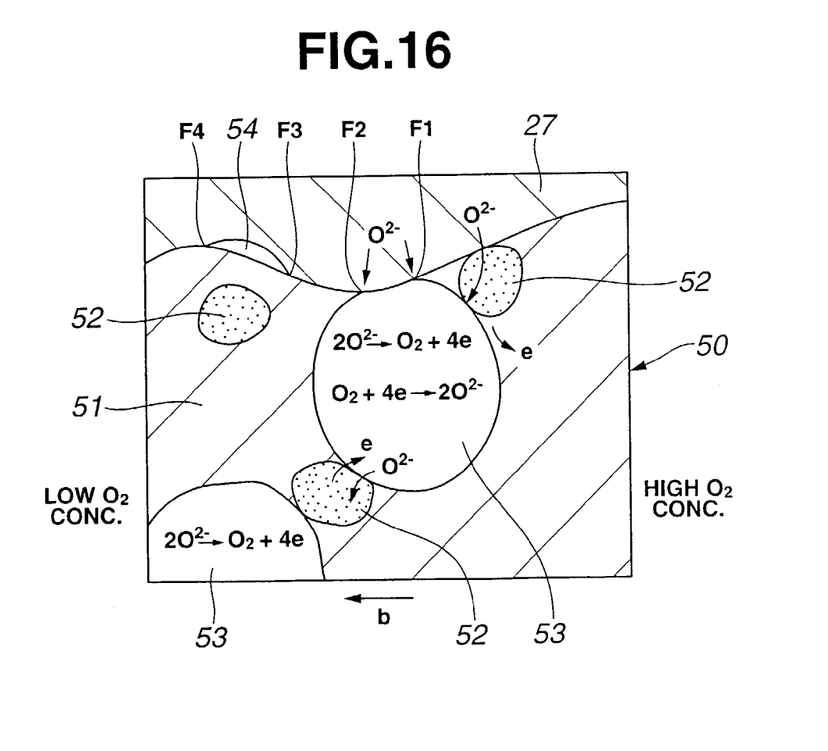
FIG. 16 is a further enlarged, schematic view of a section designated by "a" in FIG. 15.

With reference to FIGS. 15–16, there will be described a second embodiment of the present invention, which is characterized in that the ceramic material of the inner electrode is made of an oxide having a perovskite structure (mixed conductive material). In the following, the same parts as those of the first embodiment are designated by the same numerals, and their explanations are omitted.

Designated by numeral 50 is an inner electrode (first electrode) used in the second embodiment. Similar to the first embodiment, inner electrode 50 is formed of noble metal material (e.g., platinum) 51, ceramic grains 52 and void spaces 53.

Similar to recesses 44 of the first embodiment, there are provided a plurality of recesses 54 on the boundary of inner electrode 50 and solid electrolyte 27.

For example, perovskite oxide, constituting ceramic grains (mixed conductive material) 52, may have a structure of $La_{1-x}Sr_xCoO_3$ or $La_{1-x}Sr_xMnO_3$.

As shown in FIG. 16, ceramic grains 52 serve to conduct oxygen ions ($O^{2-}$) at the interface between ceramic grains 52 and solid electrolyte layer 27 and to generate the electrode reactions of the reaction formulas (1) and (2) at the interface between ceramic grains 52 and void spaces 53.

Furthermore, as shown in FIG. 16, there also occurs the electrode reaction at three-phase interfaces F1, F2 formed among solid electrolyte layer 27, noble metal material 51 and void spaces 53 and at three-phase interfaces F3, F4 formed among solid electrolyte layer 27, noble metal material 51 and recesses 54. Void spaces 53 serve as oxygen receiving chambers, thereby diffusing oxygen in inner electrode 50 according to its concentration and pressure gradients.

In fact, the oxygen concentration of the left side (leading end side of device 21) of inner electrode 50 in FIG. 16 is lower than that of the right side (base end side of device 21). Therefore, oxygen molecules and ions are transported in the direction of arrow "b" of FIG. 16 according to their concentration gradient.

The second embodiment of the present invention can bring about advantageous effects similar to those of the first embodiment. Specifically, since ceramic grains 52 of inner electrode 50 are made of an oxide of perovskite structure in the second embodiment, it is possible to uniformly distribute many of the above-mentioned three-phase interfaces (electrode reaction points), thereby effectively generate the electrode reaction at the entirety of the electrode surface of inner electrode 50.

As mentioned above, there is a first oxygen gas transportation in which oxygen gas is transported according to its concentration gradient in inner electrode 50. Furthermore, there is a second oxygen gas transportation in the second embodiment, as explained in the following.

As shown in FIG. 16, void spaces 53 and ceramic grains 52 are continuously distributed in inner electrode 50. With this distribution, void spaces 53 contribute to oxygen transportation (in the form of oxygen molecules) by diffusion therein, and in contrast ceramic grains (mixed conductive material) 52 contribute to oxygen transportation (in the form of oxygen ions) by ionic conduction.

In other words, as schematically shown in FIG. 16, oxygen ions ($O^{2-}$) from solid electrolyte layer 27 can pass in the form of oxygen ions through the adjacent ceramic grain 52. Then, at the boundary between this ceramic grain 52 and the adjacent void space 53, oxygen ions can turn to oxygen molecules by the reaction of $2O^{2-} \rightarrow O_2 + 4e$. The resulting oxygen molecules can pass through this void space 53 by gas diffusion. Then, at the boundary between this void space 53 and the next ceramic grain 52, oxygen molecules can turn to oxygen ions by the reaction of $O_2 + 4e \rightarrow 2O^{2-}$. In this manner, oxygen can be transported through ceramic grains 52 and void spaces 53 in the second oxygen gas transportation. Therefore, it is possible to accelerate the transportation speed of oxygen gas in the direction of the arrow of "b" in FIG. 16 by the above-mentioned first and second oxygen gas transportations.

Consequently, it is possible to lower internal resistance of the device to improve low-temperature activity and the like. Furthermore, for example, it is possible to suppress exfoliation of solid electrolyte layer 27 and inner electrode 50 from each other for a long time, thereby improving reliability of the air/fuel ratio sensor.

The entire contents of basic Japanese Patent Application 2002-096102 (filed Mar. 29, 2002) of the application, of which priority is claimed, are incorporated herein by reference.

What is claimed is:

1. An air/fuel ratio detection apparatus for a gas, comprising:
    a heater portion that has an elongate cylindrical shape and heats by applying electricity to the heater portion from an outside;
    a solid electrolyte layer formed on and entirely surrounding periphery of the heater portion, the solid electrolyte layer being activated by heat from the heater portion to conduct oxygen ions through the solid electrolyte layer;
    a first electrode that is positioned between the heater portion and the solid electrolyte layer and is in contact with an inner surface of the solid electrolyte layer;
    second and third electrodes that are in contact with an outer surface of the solid electrolyte layer and are away from each other such that the solid electrolyte layer is interposed between the first and second electrodes and between the first and third electrodes;
    a first voltage applying device for applying a first voltage between the first and second electrodes;
    a second voltage applying device for applying a second voltage between the first and third electrodes, the second voltage being higher than the first voltage; and
    a diffusion layer made of a porous material, the diffusion layer covering the second electrode to adjust transmission of the gas to the second electrode.

2. An apparatus according to claim 1, wherein the second electrode is positioned closer to a leading edge of the heater portion than the third electrode is.

3. An apparatus according to claim 1, further comprising an ammeter provided between the first voltage applying device and the second electrode, for outputting the output signal as an electric current.

4. An apparatus according to claim 1, wherein the second and third electrodes are positioned to be away from each other in an axial direction of the solid electrolyte layer, and
    wherein the first electrode extends to have a length in the axial direction of the solid electrolyte layer such that the first electrode is opposed to the second and third electrodes in a radial direction of the solid electrolyte layer.

5. An apparatus according to claim 1, wherein the first electrode comprises a noble metal, ceramic grains, and voids that accommodate oxygen.

6. An apparatus according to claim 5, wherein the voids have a size larger than that of the ceramic grains.

7. An apparatus according to claim 5, wherein the ceramic grains comprise a ceramic raw material that is identical with a raw material of the solid electrolyte layer.

8. An apparatus according to claim 5, wherein the ceramic grains comprise a ceramic raw material that is an oxide having a perovskite structure.

9. An apparatus according to claim 1, wherein the heater portion comprises:
    a heater core made of a ceramic material and having a hollow cylindrical shape;
    a heater pattern formed on a peripheral surface of the heater core; and
    an insulating covering layer surrounding periphery of the heater core to cover the heater pattern.

10. An air/fuel ratio detection apparatus for a gas, comprising:
    a heater portion that has an elongate cylindrical shape and heats by applying electricity to the heater portion from an outside;
    a solid electrolyte layer formed on and entirely surrounding periphery of the heater portion, the solid electrolyte layer being activated by heat from the heater portion to conduct oxygen ions through the solid electrolyte layer;

a first electrode that is positioned between the heater portion and the solid electrolyte layer and is in contact with an inner surface of the solid electrolyte layer;

second and third electrodes that are in contact with an outer surface of the solid electrolyte layer and are away from each other such that the solid electrolyte layer is interposed between the first and second electrodes and between the first and third electrodes;

a first voltage applying device for applying a first voltage between the first and second electrodes; and a second voltage applying device for applying a second voltage between the first and third electrodes, the second voltage being higher than the first voltage, wherein the first and second voltage applying devices are configured such that the first and second voltages are adjusted to allow an output signal from the second electrode to change according to air-fuel ratio of the gas.

11. An apparatus according to claim 10, wherein the second electrode is positioned closer to a leading edge of the heater portion than the third electrode is.

12. An apparatus according to claim 10, further comprising an ammeter provided between the first voltage applying device and the second electrode, for outputting the output signal as an electric current.

13. An apparatus according to claim 10, wherein the second and third electrodes are positioned to be away from each other in an axial direction of the solid electrolyte layer, and wherein the first electrode extends to have a length in the axial direction of the solid electrolyte layer such that the first electrode is opposed to the second and third electrodes in a radial direction of the solid electrolyte layer.

14. An apparatus according to claim 10, wherein the first electrode comprises a noble metal, ceramic grains, and voids that accommodate oxygen.

15. An apparatus according to claim 14, wherein the voids have a size larger than that of the ceramic grains.

16. An apparatus according to claim 14, wherein the ceramic grains comprise a ceramic raw material that is identical with a raw material of the solid electrolyte layer.

17. An apparatus according to claim 14, wherein the ceramic grains comprise a ceramic raw material that is an oxide having a perovskite structure.

18. An apparatus according to claim 10, wherein the heater portion comprises:

a heater core made of a ceramic material and having a hollow cylindrical shape;

a heater pattern formed on a peripheral surface of the heater core; and an insulating covering layer surrounding periphery of the heater core to cover the heater pattern.

\* \* \* \* \*